(12) United States Patent
Schwarz

(10) Patent No.: US 8,208,135 B2
(45) Date of Patent: Jun. 26, 2012

(54) METHOD AND DEVICE FOR THE OPTICAL ASSESSMENT OF WELDING QUALITY DURING WELDING

(75) Inventor: Joachim Schwarz, Kleinandelfingen (CH)

(73) Assignee: Precitec Vision GmbH & Co. KG, Eschborn (DE)

( * ) Notice: Subject to any disclaimer, the term of this patent is extended or adjusted under 35 U.S.C. 154(b) by 328 days.

(21) Appl. No.: 12/440,449

(22) PCT Filed: Aug. 28, 2007

(86) PCT No.: PCT/EP2007/007506
§ 371 (c)(1),
(2), (4) Date: Apr. 20, 2009

(87) PCT Pub. No.: WO2008/028580
PCT Pub. Date: Mar. 13, 2008

(65) Prior Publication Data
US 2009/0266989 A1    Oct. 29, 2009

(30) Foreign Application Priority Data

Sep. 6, 2006 (CH) ....................... 1431/06

(51) Int. Cl.
*G01N 21/00* (2006.01)
*G01N 21/86* (2006.01)
*G01B 11/24* (2006.01)
*G01V 8/00* (2006.01)
*G06K 9/00* (2006.01)

(52) U.S. Cl. .................. 356/237.1; 356/237.2; 356/601; 250/559.04; 382/141; 382/152; 348/90

(58) Field of Classification Search ........................ None
See application file for complete search history.

(56) References Cited

U.S. PATENT DOCUMENTS

| | | | | |
|---|---|---|---|---|
| 4,734,766 A | * | 3/1988 | Shiozumi et al. | 382/141 |
| 5,040,125 A | * | 8/1991 | Okumura et al. | 700/212 |
| 5,533,146 A | * | 7/1996 | Iwai | 382/150 |
| 5,978,090 A | * | 11/1999 | Burri et al. | 356/613 |
| 6,046,431 A | * | 4/2000 | Beattie | 219/124.34 |
| 6,624,899 B1 | * | 9/2003 | Clark | 356/614 |
| 6,791,057 B1 | * | 9/2004 | Kratzsch et al. | 219/121.63 |
| 7,176,965 B1 | * | 2/2007 | Noguchi | 348/222.1 |
| 7,863,544 B2 | * | 1/2011 | Serruys et al. | 219/121.83 |
| 7,989,730 B2 | * | 8/2011 | Regaard | 219/121.83 |
| 2005/0041852 A1 | * | 2/2005 | Schwarz et al. | 382/152 |

FOREIGN PATENT DOCUMENTS

| | | | |
|---|---|---|---|
| DE | 4312241 A1 | | 10/1994 |
| DE | 19852302 A1 | * | 5/2000 |
| JP | 2000184243 A | * | 6/2000 |
| JP | 2000196924 A | * | 7/2000 |

(Continued)

*Primary Examiner* — Tarifur Chowdhury
*Assistant Examiner* — Gordon Stock, Jr.
(74) *Attorney, Agent, or Firm* — Muncy, Geissler, Olds & Lowe, PLLC

(57) ABSTRACT

In laser welding, the welding area is depicted coaxially in relation to the laser beam (3) through the laser optics (4), wherein not only a triangulation line and a grey or color image of the solidified weld is recorded but also the process radiation of the welding process. From these three image elements, an optimum quality assessment of the welding process and of the weld can be made.

13 Claims, 2 Drawing Sheets

FOREIGN PATENT DOCUMENTS

| | | | |
|---|---|---|---|
| JP | 2000271743 A | | 10/2000 |
| JP | 2001287064 A | * | 10/2001 |
| JP | 2005111538 A | * | 4/2005 |
| WO | WO 0126859 A1 | * | 4/2001 |
| WO | WO 03041902 A1 | * | 5/2003 |
| WO | WO-2007/053973 A1 | | 5/2007 |

* cited by examiner

METHOD AND DEVICE FOR THE OPTICAL ASSESSMENT OF WELDING QUALITY DURING WELDING

REFERENCE TO RELATED APPLICATIONS

This application claims the priority of Swiss Patent Application no. 1431/06 that was filed on Sep. 6, 2006 and whose entire disclosure is hereby incorporated by reference.

BACKGROUND

The invention relates to a method for the optical assessment of welding quality, in particular in the case of laser welding where an image of the welding zone is recorded. The invention also relates to an apparatus for carrying out the method.

PRIOR ART

It is known to test welds optically. In particular, to this end 2D laser scanners are used to lay a laser light line (laser triangulation line) transversely over the weld, and geometric data of the weld are determined therefrom. Furthermore, it is known from JP 2005111538 to record the image of the molten metal during laser welding and to compare it with reference data.

SUMMARY OF THE INVENTION

The invention is based on the object of improving the optical quality testing of welds.

This is achieved in the case of the method mentioned at the beginning by virtue of the fact that in this case the process illumination, on the one hand, and also a gray or color image of the solidified weld and the laser triangulation line, on the other hand, are recorded in different image regions.

The quality assessment of welding can be carried out optimally during the welding process by three different image elements on the image with the two image regions.

In a preferred design of the invention, the different image elements are recorded on a single sensor that has a plurality of image regions on which it is possible to record (Multiple Regions of Interest, MROI). It is then necessary merely to read out this one sensor in order to be able to evaluate all the image regions with the three image elements of the image. During recording, a first image region with the process illumination is preferably recorded with an exposure time of 5 µsec or less. The first image region, on which the process illumination is recorded as image element, is preferably configured with a logarithmic characteristic of the sensor.

Furthermore, it is preferred to provide a second image region on which the image element of the laser triangulation line and the image element of the gray or color image of the weld are recorded together. By way of example, in this case the second image region is recorded with an exposure time of approximately 10 µsec and is illuminated with an illumination period by a flashlight source of less than 10 µsec. It is further preferred that the recording parameters for recording of the first and the second image region are altered between the recordings. In a preferred embodiment, a planar optics with different transparency regions for the first and the second sensor region or image region is provided, particularly directly above the sensor chip.

It is further preferred that the recording is performed through the laser optics of the welding laser, and this produces a particularly compact arrangement. In the case of arc welding, or MIG/MAG welding, use is made of an optics arranged next to the torch.

The invention is further based on the object of providing an apparatus for carrying out the method. Said apparatus is designed in accordance with the corresponding apparatus claim.

BRIEF DESCRIPTION OF THE DRAWINGS

Further refinements, advantages and applications of the invention emerge from the dependent claims and from the description now following with the aid of the figures, in which:

WAYS OF IMPLEMENTING THE INVENTION

Figure 1:
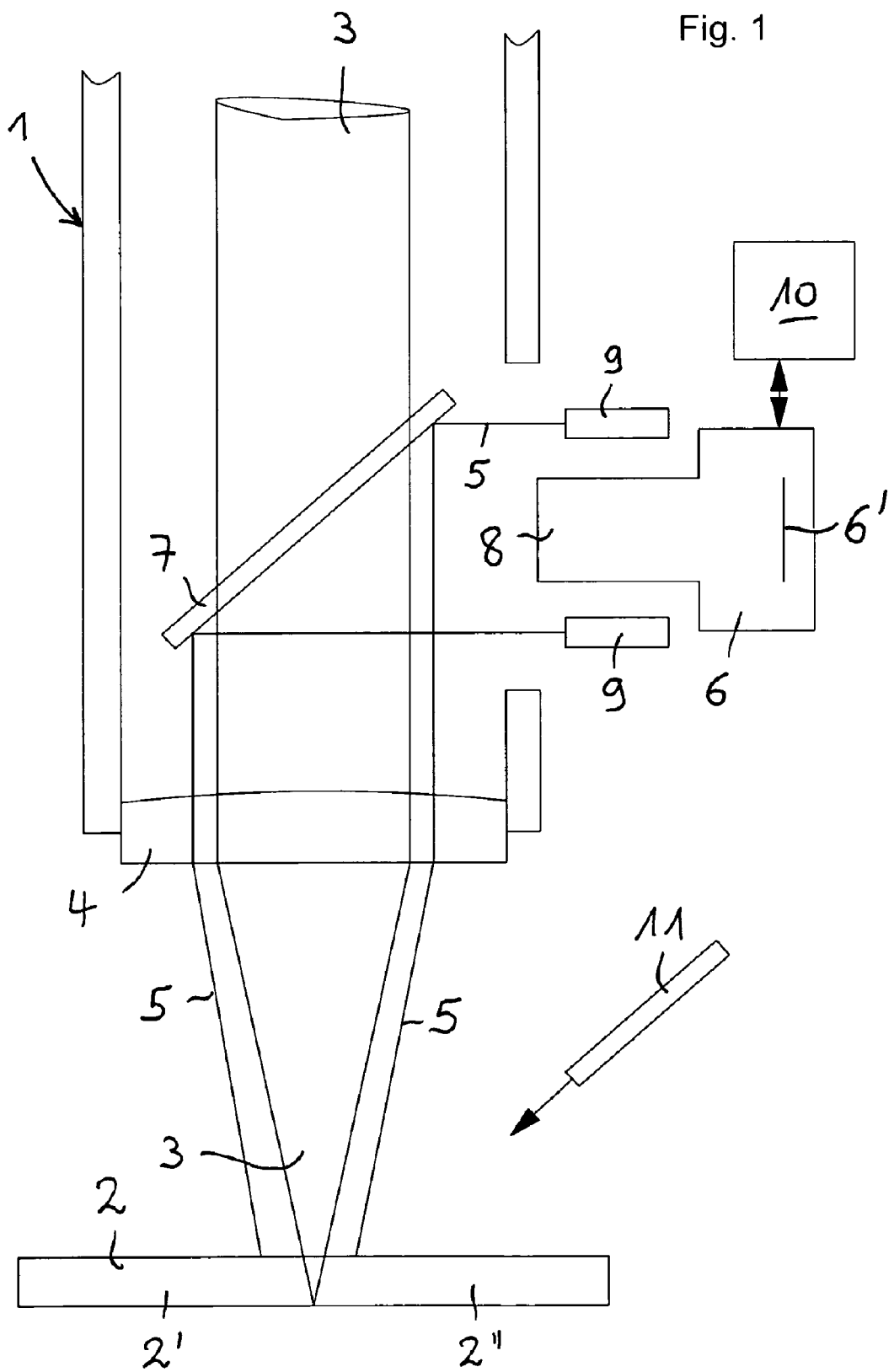
FIG. 1 is a schematic of a welding head with a camera arranged thereon.

FIG. 1 shows a highly schematic view of a welding head 1 that is arranged above the weld metal 2 that in this example consists of two sheets 2' and 2" to be welded. The welding torch is formed in this preferred case by a laser beam 3 that, through an optics 4, strikes through the weld metal 2 and executes the welding there. In accordance with the invention, it is also possible to assess other welding methods than laser welding, thus in particular welding with the aid of all known arc methods. The welding is preferably performed as MIG/MAG welding with appropriate gas feed, but this is not illustrated in the schematic of FIG. 1. A camera 6 views the welding area on the weld metal 2. The camera is preferably a highly dynamic CMOS camera and, in particular, a camera that is configured to record a plurality of images on the sensor chip (something which is also known as MROI (Multiple Regions of Interest)), these being output as an image. In particular, a camera of type Photonfocus Hurricane, MV-1024 CL-80/160 from Photonfocus AG, CH-8853 Lachen, Switzerland can be used; this is equipped with MROI and enables different exposure times for the various regions. However, it is also possible to use two cameras and/or two sensors. However, the recording is preferably performed by one camera and, in particular, by a camera 6 that is arranged directly on the welding head. The recording is preferably performed directly through the optics 4 for the laser beam, as illustrated in the example shown. Through a beam splitter 7 for the visible light viewed by the camera 6, the light emanating from the weld metal 2 passes through the camera optics 8 onto the CMOS sensor 6' thereof. 9 denotes an illumination intended to illuminate the recorded region and which preferably illuminates the weld metal 2 via the beam splitter 7. The corresponding beam path for the illumination is denoted by 5. This illumination is a xenon flash illumination or an LED illumination, in particular an illumination with surface emitting laser diodes (Vertical Cavity Surface Emitting Laser/VCSEL). These diodes have the property of high optical power in conjunction with low packing density and low beam divergence, and can illuminate the welding area with adequate brightness. The recording of the welding area through the welding optics 4 for all the regions to be recorded in accordance with the invention requires very high luminance levels, since the sensor parameters of the CMOS sensor are set to be optically insensitive in order to be able to record very bright process illuminations, and the laser optics has poor transparency properties for visible light. The region shown, in the case of which the camera 6 views the welding area through the welding optics 4, is, nevertheless, the preferred arrangement even if other arrangements in the case of which the camera does not view the welding area through the laser optics 4 are likewise possible. As may be seen in the following figures, at least one triangulation line is projected over the solidified weld by means of a known arrangement 11 with a further laser. A controller and/or evaluation circuit 10, which is formed as a rule by a computer, receives the image data read out from the camera for the purpose of evaluating them. In the case of arc welding (MIG/MAG welding), the recording is performed with a camera having an optics arranged near the welding torch, and which is not further explained here.

Figure 2:
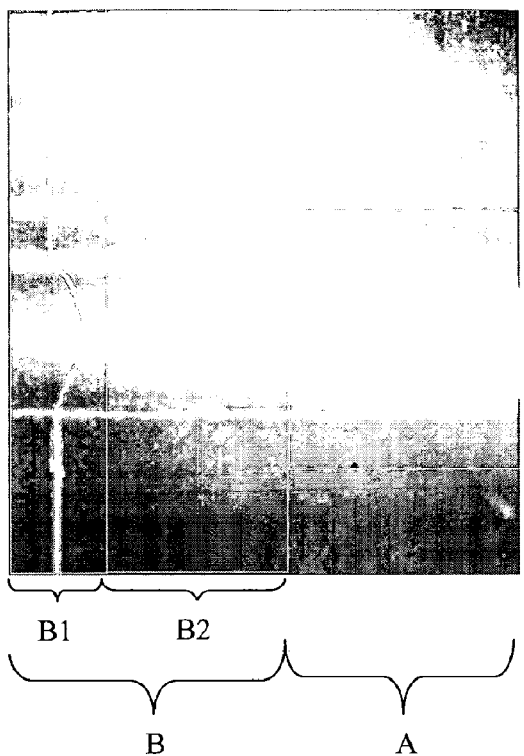
FIG. 2 shows an image, recorded in accordance with the invention, of a weld free from defects.

FIG. 2 shows an example of a recorded image of the welding area, this being a defect-free weld. FIG. 2 shows in this case a recording with a large object field of the camera such that the process illumination and the weld already solidified after the process can be recorded on the same sensor as the image, be read out as an image, and subsequently be tested. Here, process illumination or process light evaluation is understood as the recording and the evaluation of the welding area with still liquid welding material shining in the visible region. According to the invention, three different image elements are recorded. The detection of the local flaws of the weld is performed in this case with the laser triangulation which is known per se and for which purpose the triangulation line correspondingly projected over the weld is recorded, and with the aid of a gray image analysis or possibly a color image analysis, to which end the image of the weld is recorded. The process illumination is recorded in addition. It is possible to proceed such that the sensor 6' of the camera is divided into two main regions A and B. These can be, in particular, two separately exposable regions on the same camera sensor 6'. In the main region A in accordance with FIG. 2 for the purpose of visualizing the process illumination the sensor region is operated with a logarithmic characteristic and with exposure times of preferably less than 5 μs. In the main region B, operation is by way of a linear or logarithmic characteristic and exposure times in the range of 10 μs, in order to record the triangulation line in region B1 as image element, and the image of the weld in region B2 as further image element. The exposure time is selected in this case such that the triangulation line in region B1 is explained sufficiently brightly for the purpose of evaluation, but that excessive irradiation by the process illumination is prevented. In this exposure time, a light pulse with a duration of <10 μs illuminates with the aid of a flashlight source or of the abovementioned VCSEL light sources. The xenon flashlight source used in the optical weld inspection device SOUVIS 5000 from Soudronic AG, Bergdietikon, Switzerland can be operated with a pulse duration of from 5 μs to 10 μs, and be used therefor, and illuminates the weld sufficiently brightly. The short flash duration prevents movement unsharpness in this case. The camera parameters are preferably switched over for the recording of the two regions in order to optimize the recording situation depending on the region. It is possible to make use for this purpose of the Soudronic fast track camera module from Soudronic AG, Bergdietikon, Switzerland, which permits the camera parameters to be switched over quickly and likewise permits the two regions of the CMOS sensor 6' to be read out quickly, said module cooperating with the abovementioned Hurricane camera from Photonfocus. An appropriate control for the camera is indicated in FIG. 1 by 10. Furthermore, in order to record the regions A and B it is preferred to subdivide the sensor with a planar optics directly on the sensor chip or at a spacing from the latter into two regions of different sensitivity in accordance with the regions A and B of FIG. 2. The planar optics can consist of a cover glass with two regions of different transparency. The transparency can in this case be 100% for the region B for the purpose of evaluating geometry and gray image, and less than 50% for the purpose of evaluating process light and/or the region A.

Figure 3:
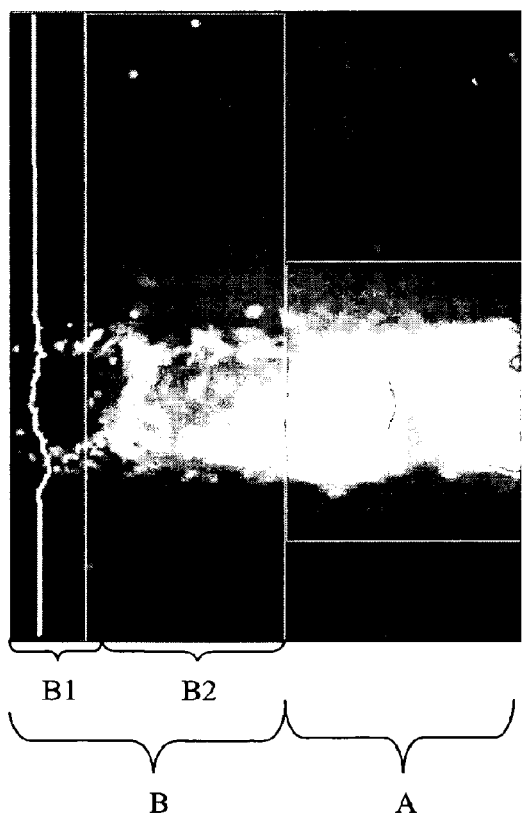
FIG. 3 shows an image, recorded in accordance with the invention, with a welding defect caused by a welding wire defect.

FIG. 3 shows a record that was executed in the abovementioned way and like that of FIG. 2, although here a welding defect caused by a defect in the welding wire has occurred during welding. It is to be seen that, on the one hand, in the region B1 of the main region B the triangulation identifies the weld defect in the solidified region. On the other hand, a corresponding roughness of the weld is also to be effected in the gray image record in the region B2 of the main region B. It is therefore possible straight away to locate the weld defect by an evaluation that can also take place in the controller 10 or in a separate computer. Furthermore, deviation from the normal image as was illustrated in FIG. 2 is likewise clearly to be detected in the region A, in which the process illumination was recorded. This, as well, can be located straight away by an image evaluation and be used to control the quality of the welding operation. In the case of process illumination, the camera respectively sees a typical light distribution in the visible region, as is clearly evident in FIG. 2, which light distribution is disturbed in the presence of a defective weld, as may be seen in FIG. 3. By recording the laser line and the gray image in the region B, it is further possible in a known way to measure the weld width and the weld position, and measure the geometric data such as convexity, concavity and, if appropriate, an edge misalignment. Furthermore, the weld volume can be measured in a known way. The measurement of the geometric data is performed in this case via laser triangulation, and the detection of local and global defective places is performed via gray image analysis and laser triangulation.

The evaluation of the process illumination for intensity and geometric features together with the geometric measurement with the aid of weld and gray image analysis in this case yields a reliable statement on the quality of the weld. The rapid switching over of the sensor regions A and B renders possible optimum sensor characteristics and/or camera parameters for the different tasks set for the two records on the two sensor regions. All the recordings are preferably executed with the aid of only one sensor, and this substantially reduces the outlay on apparatus, the outlay on operation and the outlay on maintenance. Owing to the arrangement of the sensor and/or the camera directly on the welding torch, substantially less outlay is required than for a separate treatment in a separate welding test. The present invention can be used in monitoring the quality of welds, in particular MIG/MAG welds of all types, and also for monitoring the geometry of surfaces while simultaneously inspecting the surface condition and monitoring the welding process.

While preferred designs of the invention are described in the present application, it is expressly to be pointed out that the invention is not restricted to these and can also be executed in another way within the scope of the following claims.

The invention claimed is:

1. A method for optical assessment of welding quality during welding in which a welding zone is observed by an optical sensor, and a laser triangulation line is laid over an already solidified part of the weld, characterized in that a process illumination of a still liquid welding material shining in the visible region, and a gray or color image of a solidified weld and the laser triangulation line are recorded in different image regions, with the different image regions recorded on a single sensor and read out as an image, wherein a recording of a first image region with the process illumination is performed separately from a recording of a second image region with the triangulation line and the gray or color image, wherein the different image regions are read out with different exposure times, wherein the second image region comprises a subregion containing the laser triangulation line, and a subregion containing the gray or color image, which are recorded together, and wherein the second image region is recorded with an exposure time of approximately 10 μsec and is illuminated with an illumination period by a flashlight source of less than 10 μsec.

2. The method as claimed in claim 1, wherein the recording of the first image region for the process illumination is performed with an exposure time of 5 μsec or less.

3. The method as claimed in claim 1, wherein the recording of the first image region for the process illumination is performed with a logarithmic characteristic of the single sensor.

4. The method as claimed in claim 1, wherein recording parameters for recording of the different image regions are altered between the recordings.

5. The method as claimed in claim 1, wherein the recording of the first and second image regions is performed through an optic of a welding laser.

6. The method as claimed in claim 1, wherein a planar optic of different transparency for the first and second image regions is provided above the single sensor, directly on a sensor chip.

7. The method as claimed in claim 1, wherein the welding is laser welding or arc welding.

8. An apparatus for carrying out the method as claimed in claim 1, wherein a welding fixture, having a laser beam source, a laser for projecting a light triangulation line, and a camera that is arranged on a welding device, views a welding area, and is arranged and configured to record the process illumination and the subsequent solidified weld region.

9. The apparatus as claimed in claim 8, wherein the camera views the welding area through a welding optic via a beam splitter.

10. The apparatus as claimed in claim 8, wherein a flashlight illumination with surface emitting laser diodes is provided.

11. The apparatus as claimed in claim 8, wherein the recording of the first image region for the process illumination is performed with an exposure time of 5 μsec or less.

12. The apparatus as claimed in claim 9, wherein the recording of the first image region for the process illumination is performed with a logarithmic characteristic of the single sensor.

13. The apparatus as claimed in claim 8, wherein recording parameters for recording of the different image regions are altered between the recordings.

* * * * *